Figure 1:
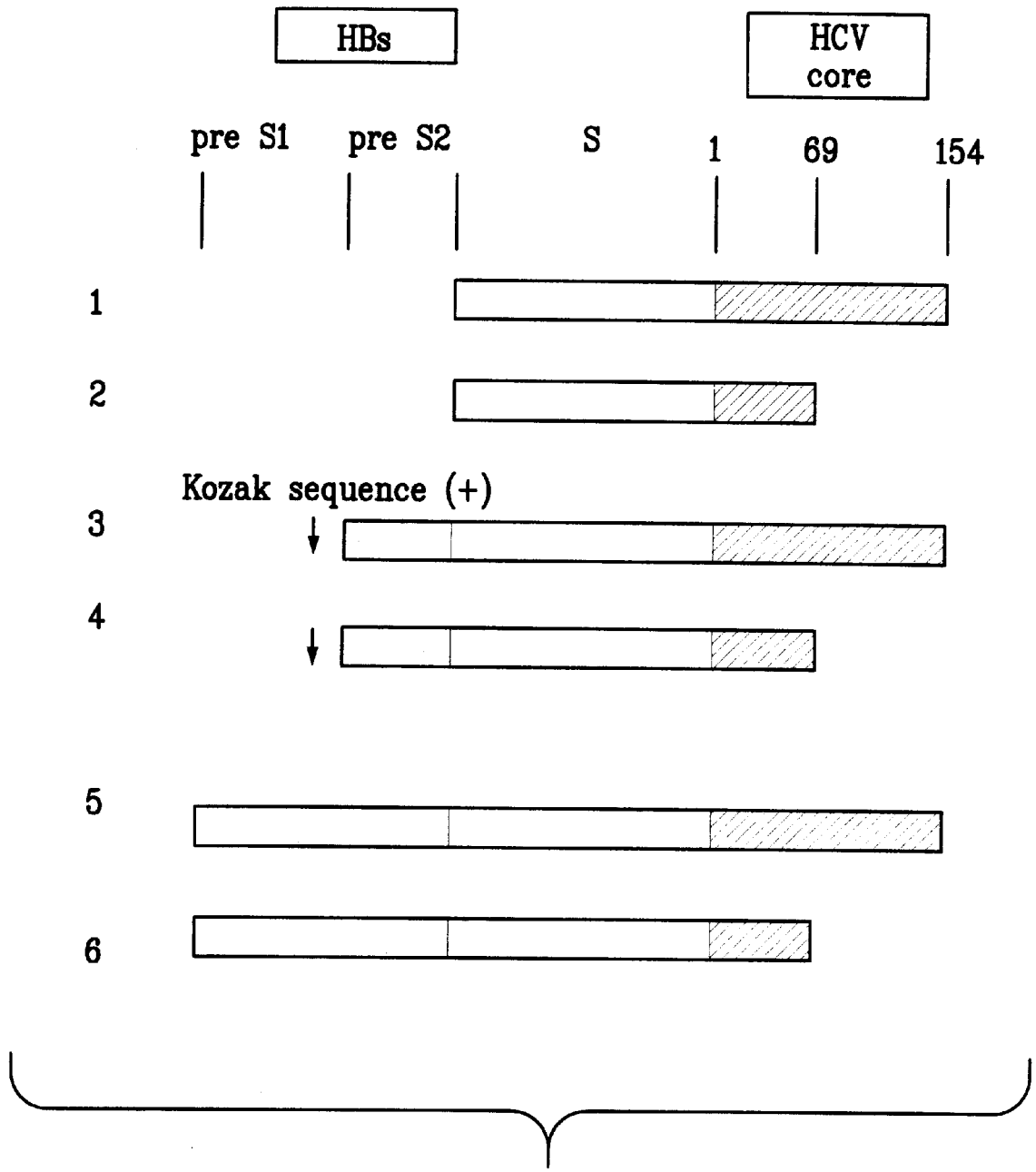

US006025341A

United States Patent [19]
Wands et al.

[11] Patent Number: 6,025,341
[45] Date of Patent: Feb. 15, 2000

[54] CHIMERIC HEPATITIS B/HEPATITIS C VIRUS VACCINE

[75] Inventors: Jack R. Wands, Waban; Katsutoshi Tokushige, Boston, both of Mass.; Takaji Wakita, Tokyo, Japan

[73] Assignee: The General Hospital Corporation, Charlestown, Mass.

[21] Appl. No.: 08/854,531

[22] Filed: May 12, 1997

Related U.S. Application Data

[63] Continuation of application No. 08/467,859, Jun. 6, 1995, abandoned.
[51] Int. Cl.[7] ............................ C12N 15/11; C07K 14/00; A61K 48/00
[52] U.S. Cl. ............................ 514/44; 536/23.1; 530/350
[58] Field of Search ............................ 514/44; 536/23.1; 435/320.1; 424/135.1; 530/350

[56] References Cited

U.S. PATENT DOCUMENTS

| | | | |
|---|---|---|---|
| 5,196,194 | 3/1993 | Rutter et al. | 424/189.1 |
| 5,204,096 | 4/1993 | Neurath et al. | 424/189.1 |
| 5,589,466 | 12/1996 | Felgner et al. | 514/44 |
| 5,593,972 | 1/1997 | Weiner et al. | 514/44 |

FOREIGN PATENT DOCUMENTS

| | | |
|---|---|---|
| 2055149 | 5/1992 | Canada . |
| 0278940 | 8/1988 | European Pat. Off. . |
| 6-92996 | 4/1994 | Japan . |
| 6141870 | 5/1994 | Japan . |
| WO 93/15193 | 8/1993 | WIPO . |
| WO 93/15207 | 8/1993 | WIPO . |
| 6141870 | 5/1994 | WIPO . |
| WO 94/16737 | 8/1994 | WIPO . |

OTHER PUBLICATIONS

Alter, M. et al., "The Natural History of Community–Acquired Hepatitis C in the United States", *N. Eng. J. of Medicine*, 1992, 327(27), 1899–1905.

Barry, M. et al., "Production of Monoclonal Antibodies by Genetic Immunization", *BioTechniques*, 1994, 16(4), 616, 618–19.

Bartenschlager, R. et al., "Nonstructural Protein 3 of the Hepatitis C Virus Encodes a Serine–Type Proteinase Required for Cleavage at the NS3/4 and NS4/5 Junctions", *J. of Virol.*, 1993, 67, 3835–3844.

Blum, H. et al., "Hepatitis B Virus X Protein is not Central to the Viral Life Cycle in Vitro", *J. of Virol.*, 1992, 66, 123–127.

Blum, H. et al., "Persistence of Hepatitis B Viral DNA After Seroligical Recovery from Hepatitis B Virus Infection", *Hepatology*, 1991, 14(1), 56–63.

Botarelli, P. et al., "T–Lymphocyte Response to Hepatitis C Virus in Different Clinical Courses of Infection", *Gastroenterology*, 1993, 104, 580–587.

Chen, H.–S. et al., "The Woodchuck Hepatitis Virus X Gene is Important for Establishment of Virus Infection in Woodchuck", *J. Virology*, 1993, 67(3), 1218–1226.

Chiba, J. et al., "Serodiagnosis of Hepatitis C Virus (HCV) Infection with an HCV Core Protein Molecularly Expressed by a Recombinant Baculovirus", *PNAS USA*, 1991, 88, 4641–4645.

Choo, Q.–L. et al., "Genetic Organization and Diversity of the Hepatitis C Virus", *PNAS USA*, 1991, 88, 2451–2455.

Bukh, J. et al., "Sequence Analysis of the Core Gene of 14 Hepatitis C Virus Genotypes", *PNAS USA*, 1994, 91, 8239–8234.

Bukh, J. et al., "Sequence Analysis of the 5' Noncoding Region of Hepatitis C Virus", *PNAS USA*, 1992, 89, 4942–4946.

Colombo, M. et al., "Prevalence of Antibodies to Hepatitis C Virus in Italian Patients with Hepatocellular Carcinoma", *The Lancet*, Oct. 28, 1989, 1006–1008.

Cox, G. et al., "Bovine Herpesvirus 1: Immune Responses in Mice and Cattle Injected with Plasmid DNA", *J. Virology*, 1993, 67(9), 5664–5667.

Davis, H. et al., "DNA–based Immunization Induces Continuous Secretion of Hepatitis B Surface Antigen and High Levels of Circulating Antibody", *Human Molecular Genetics*, 1993, 2(11), 1847–1851.

Farci, P. et al., "Lack of Protective Immunity Against Reinfection with Hepatitis C Virus", *Science*, 1992, 258, 135–140.

Ferrari, C. et al., "T–cell Response to Structural and Nonstructural Hepatitis C Virus Antigens in Persistent and Self–limited Hepatitis C Virus Infections", *Hepatology*, 1994, 19(2), 286–295.

Fynan, E.F. et al., "Use of DNA Encoding Influenza Hemagglutinin as an Avian Influenza Vaccine", *DNA and Cell Biology*, 1993, 12(9), 785–789.

Ganem, D. and Varmus, "The Molecular Biology of the Hepatitis B Viruses", *Ann. Rev. Biochem.*, 1987, 56, 651–693.

Grakoui, A. et al., "Characterization of the Hepatitis C Virus–Encoded Serine Proteinase: Determination of Proteinase–Dependent Polyprotein Cleavage Sites", *J. of Virol.*, 1993, 67, 2823–2843.

(List continued on next page.)

*Primary Examiner*—Bruce R. Campell
*Assistant Examiner*—Deborah J. R. Clark
*Attorney, Agent, or Firm*—Woodcock Washburn Kurtz Mackiewicz & Norris LLP

[57] ABSTRACT

Nucleic acid molecule that comprise an incomplete hepatitis C and hepatitis B viral genome including specifically disclosed DNA sequences are disclosed. Pharmaceutical compositions that contain nucleic acid molecules comprising an incomplete hepatitis C and hepatitis B viral genome including a nucleotide sequence encoding a complete hepatitis C core protein and hepatitis B S gene protein operably linked to regulatory elements functional in human cells are disclosed. Methods of immunizing individuals susceptible to or infected by hepatitis B virus and/or hepatitis C virus comprising the step of administering such pharmaceutical compositions are disclosed.

60 Claims, 3 Drawing Sheets

OTHER PUBLICATIONS

Han, J.H. et al., "Characterization of the Terminal Regions of Hepatitis C Viral RNA: Identification of Conserved Sequences in the 5' Untranslated Region and Poly(A) Tails at the 3' End", *PNAS USA*, 1991, 88, 1711–1715.

Heinz, F.X., "Comparative Molecular Biology of Flaviviruses and Hepatitis C Virus", *Arch. Virol.*, 1992, 4, 163–171.

Hijikata, M. et al., "Gene Mapping of the Putative Structural Region of the Hepatitis C Virus Genome by in vitro Processing Analysis", *PNAS USA*, 1991, 88, 5547–5551.

Hosein, B. et al., "Improved Serodiagnosis of Hepatitis C Virus Infection with Synthetic Peptide Antigen from Capsie Protein", *PNAS USA*, 1991, 88, 3647–3651.

Houghton, M. et al., "Molecular Biology of the Hepatitis C Viruses: Implications for Diagnosis, Development and Control of Viral Disease", *Hepatology*, 1991, 14, 381–388.

Hsu, H. et al., "Characterization of Hepatitis C Virus Structural Proteins with a Recombinant Baculovirus Expression System", *Hepatology*, 1993, 17, 763–771.

Inchauspe, G. et al., "Genomic Structure of the Human Prototype Strain H of Hepatitis C Virus: Comparison with American and Japanese Isolates", *PNAS USA*, 1991, 88, 10292–10296.

Katayama, T. et al., "Improved Serodiagnosis of Non–A, Non–B Hepatitis by an Assay Detecting Antibody to Hepatitis C Virus Core Antigen", *Hepatology*, 1992, 15, 391–394.

Kato, N. et al., "Characterization of Hypervariable Regions in the Putative Envelope Protein of Hepatitis C Virus", *Biochem. and Biophys. Res. Comm.*, 1992, 189(1), 119–127.

Kato, N. et al., "Molecular Cloning of the Human Hepatitis C Virus Genome from Japanese Patients with Non–A, Non–B Hepatitis", *PNAS USA*, 1990, 87, 9524–9528.

Kita, H. et al., "HLA B44–restricted Cytotoxic T Lymphocytes Recognizing and Epitope on Hepatitis C Virus Nucleocapsid Protein", *Hepatology*, 1993, 18, 1039–1044.

Korba, B. et al., "Hepatocellular Carcinoma in Woodchuck Hepatitis Virus–Infected Woodchucks: Presence of Viral DNA in Tumor Tissue from Chronic Carriers and Animals Serologically Recovered from Acute Infections", *Hepatology*, 1989, 9(3), 461–470.

Korba, B. et al., "Natural History of Woodchuck Hepatitis Virus Infections During the Course of Experimental Viral Infection: Molecular Virologic Features of the Liver and Lymphoid Tissues", *J. Virology*, 1989, 63(3), 1360–1370.

Koziel, M. et al., "Hepatitis C Virus (HCV)–Specific Cytotoxic T Lymphocytes Recognize Epitopes in the Core and Envelope Proteins of HCV", *J. Virology*, 1993, 67(12), 7522–7532.

Koziel, M. et al., "Intrahepatic Cytotoxic T Lymphocytes Specific for Hepatitis C Virus in Persons with Chronic Hepatitis", *The J. of Immunology*, 1992, 149, 3339–3344.

Manthorpe, M. et al., "Gene Therapy by Intramuscular Injection of Plasmid DNA: Studies on Firefly Luciferase Gene Expression in Mice", *Human Gene Therapy*, 1993, 4, 419–431.

Martell, M. et al., "Hepatitis C Virus (HCV) Circulates as a Population of Different but Closely Related Genomes: Quasispecies Nature of HCV Genome Distribution", *J. Virology*, 1992, 66(5), 3225–3229.

Montgomery, D. et al., "Heterologous and Homologous Protection Against Influenza A by DNA Vaccination: Optimization of DNA Vectors", *DNA and Cell Biology*, 1993, 12(9), 777–783.

Nasoff, M. et al., "Identification of an Immunodominant Epitope Within the Capsid Protein of Hepatitis C Virus", *PNAS USA*, 1991, 88, 5462–5466.

Okamoto, H. et al., "Antibodies Against Synthetic Oligopeptides Deduced from the Putative Core Gene for the Diagnosis of Hepatitis C Virus Infection", *Hepatology*, 1992, 15, 180–186.

Okamoto, H. et al., "Nucleotide Sequence of the Genomic RNA of Hepatitis C Virus Isolated from a Human Carrier: Comparison with Reported Isolates for Conserved and Divergent Regions", *J. Gen. Virol.*, 1991, 72, 2697–2704.

Okamoto, H. et al., "Typing Hepatitis B Virus by Homology in Nucleotide Sequence: Comparison of Surface Antigen Sybtypes", *J. Gen. Virol.*, 1988, 69, 2575–2583.

Saito, I. et al., "Hepatitis C Virus Infection is Associated with the Development of Hepatocellular Carcinoma", *PNAS USA*, 1990, 87, 6547–6549.

Schupper, H. et al., "Peripheral–blood Mononuclear Cell Responses to Recombinant Hepatitis C Virus Antigens in Patients with Chronic Hepatitis C", *Hepatology*, 1993, 18, 1055–1060.

Selby, M. et al., "Expression, Identification and Subcellular Localization of the Proteins Encoded by the Hepatitis C Viral Genome", *J. Gen. Virol.*, 1993, 74, 1103–1113.

Santolini, E. et al., "Biosynthesis and Biochemical Properties of the Hepatitis C Virus Core Protein", *J. Virology*, 1994, 68(6), 3631–3641.

Schödel, F. et al., "The Biology of Avian Hepatitis B Viruses", Chapter 3 in "Molecular Biology of the Hepatitis B Virus", 1991, vol. 3, CRC Press, Boca Raton, FL, pp. 53–80.

Schek, N. et al., "The Hepadnaviral X Protein", Chap. 9 in "Molecular Biology of the Hepatitis B Virus", 1991, vol. 3, CRC Press, Boca Raton, FL, pp. 53–80.

Shih, C.–M. et al., "Suppression of Hepatitis B Virus Expression and Replication by Hepatitis C Virus Core Protein in HuH–7 Cells", *J. of Virol.*, 1993, 67(10), 5823–5832.

Shirai, M. et al., "An Epitope in Hepatitis C Virus Core Region Recognized by Cytotoxic T Cells in Mice and Humans", *J. Virology*, 1994, 68(5), 3332–3342.

Simmonds, P. et al., "Classification of Hepatitis C Virus into Six Major Genotypes and a Series of Subtypes by Phylogenetic Analysis of the NS–5 Region", *J. Gen. Virol.*, 1993, 74, 2391–2399.

Simonetti, R. G. et al., "Hepatitis C Virus Infection as a Risk Factor for Hepatocellular Carcinoma in Patients with Cirrhosis", *Annals of Internal Medicine*, 1992, 116(2), 97–102.

Takamizawa, A. et al., "Structure and Organization of the Hepatitis C Virus Genome Isolated from Human Carriers", *J. of Virol.*, 1991, 65, 1105–1113.

Tang, D. et al., "Genetic Immunization is a Simple Method for Eliciting an Immune Response", *Nature*, 1992, 356, 152–154.

Tsukuma, H. et al., "Risk Factors for Hepatocellular Carcinoma Among Patients with Chronic Liver Disease", *N. Eng. J. of Med.*, 1993, 328(25), 1797–1801.

Ulmer, J. et al., "Heterologous Protection Against Influenza by Injection of DNA Encoding a Viral Protein", *Science*, 1993, 259, 1745–1749.

Valenzuela, P. et al., "The Nucleotide Sequence of the Hepatitis B Viral Genome and the Identification of the Major Viral Genes", in "Animal Virus Genetics", Fields, B. et al., eds., Academic Press, NY, 1980, pp. 57–70.

Wakita, T. et al., "Specific Inhibition of Hepatitis C Virus Expression by Antisense Oligodeoxynucleotides", *J. Biol. Chem.*, 1994, 269, 14205–14210.

Wang, B. et al., "DNA Inoculation Induces Neutralizing Immune Responses Against Human Immunodeficiency Virus Type 1 in Mice and Nonhuman Primates", *DNA and Cell Biology*, 1993, 12(9), 799–805.

Wang, C. et al., "Translation of Human Hepatitis C Virus RNA in Cultured Cells is Mediated by an Internal Ribosome–Binding Mechanism", *J. Virology*, 1993, 67(6), 3338–3344.

Wang, B. et al., "Gene Inoculation Generates Immune Responses Against Human Immunodeficiency Virus Type 1", *PNAS USA*, 1993, 90, 4156–4160.

Weiner, A. et al., "Variable and Hypervariable Domains are Found in the Regions of HCV Corresponding to the Favivirus Envelope and NS1 Proteins and the Pestivirus Envelope Glycoproteins", *Virology*, 1991, 180, 842–848.

Weiner, A. et al., "Evidence for Immune Selection of Hepatitis C Virus (HCV) Putative Envelope Glycoprotein Variants: Potential Role in Chronic HCV Infections", *PNAS USA*, 1992, 89, 3468–3472.

Wolff, J. et al., "Direct Gene Transfer into Mouse Muscle in Vivo", *Science*, 1990, 247, 1465–1468.

Wolff, J. et al., "Long–term Persistence of Plasmid DNA and Foreign Gene Expression in Mouse Muscle", *Human Molecular Genetics*, 1992, 1(6), 363–369.

Xiang, Z. et al., "Vaccination with a Plasmid Vector Carrying the Rabies Virus Glycoprotein Gene Induces Protective Immunity against Rabies Virus", *Virology*, 1994, 199, 132–140.

Wang, Y. et al., "Prevalence, Genotypes, and Isolate (HC–C2) of Hepatitis C Virus in Chinese Patients with Liver Disease", *J. of Medical Virology* 1993, 40, 254–260.

Chisari, F. et al., "Molecular Pathogenesis of Hepatocellular Carcinoma in Hepatitis B Virus Transgenic Mice", *Cell*, 1989, 59, 1145–1156.

Chisari, F. et al., "Structural and Pathological Effects of Synthesis of Hepatitis B Virus Large Envelope Polypeptide in Transgenic Mice", *PNAS USA*, 1987, 84, 6909–6913.

Guidotti, L. et al., "Cytotoxic T. Lymphocytes Inhibit Hepatitis B Virus Gene Expression by a Noncytolytic Mechanism in Transgenic Mice", *PNAS USA*, 1994, 91, 3764–3768.

Guidotti, L. et al., "Intracellular Inactivation of the Hepatitis B Virus by Cytotoxic T Lymphocytes", *Immunity*, 1996, 4, 25–36.

Marquardt, O. et al., "Cell Type Specific Expression of Pre S1 Antigen and Secretion of Hepatitis B Virus Surface Antigen", *Arch. Virol.*, 1987, 98, 249–256.

Moriyama, T. et al., "Immunobiology and Pathogenesis of Hepatocellular Injury in Hepatitis B Virus Transgenic Mice", *Science*, 1990, 361–364.

Persing, D. et al., "Inhibition of Secretion of Hepatitis B Surface Antigen by a Related Presurface Polypeptide", *Science*, 1986, 234, 1388–1391.

Santolini, E. et al., "Biosynthesis and Biochemical Properties of the Hepatitis C Virus Core Protein", *J. Virology*, 1994, 68(6), 3631–3641.

Wells, *FEBS*, 1993, 332, 179–182.

Farci et al., *Clinical and Experimental Rheumatology*, Nov. 1995, 13 (Supp. 13).

Tokushige et al., "Expression and Immune Response to Hepatitis C Virus Core DNA–Based Vaccine Constructs", *Hepatology*, 1996, 24(1), 14–20.

Chattergoon et al. Genetic immunizations: a new era in vaccines and immune therapeutics. FASEB, vol. 11, pp. 753–763, Aug. 1997.

Robinson, H. L. Nucleic acid vaccines: an overview. Vaccine, vol. 15, No. 8, pp. 785–787, 1997.

McDonnell et al. Molecular Medicine DNA Vaccines. New England Journal of Medicine, vol. 334, pp. 42–45, Jan. 4, 1996.

Major, M.E. et al., "DNA–Based Immunization with Chimeric Vectors for the Induction of Immune Responses Against the Hepatitis C Virus Nucleocapsid", *J. Virol.*, 1995, 69(9), 5798–5805.

Database WPI, JP 06 279 500 A, "Hybrid protein derived from HBc HCV hybridised gene —useful for the simultaneous detection of hepatitis B and C", 1994, XP–002072536, Abstract Only, 1 page.

Itoh et al., Proc. Nat. Acad. Sci., 83, 1986, 9174–9178.

Yoshikawa et al., J. Virology, 67(10), 1993, 6064–6070.

Wells, FEBS, 332, 1993, 179–182.

Farci et al., Clinical and Experimental Rheumatology 13 Supp. 13, Nov. 1995.

Backbone A

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 462 base pairs

```
        (B) TYPE: nucleic acid
        (C) STRANDEDNESS: double
        (D) TOPOLOGY: linear (xi) SEQUENCE DESCRIPTION: SEQ ID NO:1:

ATG AGC ACG AAT CCT AAA CCT CAA AGA AAA ACC AAA CGT AAC ACC AAC      48
Met Ser Thr Asn Pro Lys Pro Gln Arg Lys Thr Lys Arg Asn Thr Asn
 1               5                  10                  15

CGC CGC CCA CAG GAC GTC AAG TTC CCG GGC GGT GGT CAG ATC GTT GGT      96
Arg Arg Pro Gln Asp Val Lys Phe Pro Gly Gly Gly Gln Ile Val Gly
                20                  25                  30

GGA GTT TAC CTG TTG CCG CGC AGG GGC CCC AGG TTG GGT GTG CGC GCG     144
Gly Val Tyr Leu Leu Pro Arg Arg Gly Pro Arg Leu Gly Val Arg Ala
            35                  40                  45

ACT AGG AAG ACT TCC GAG CGG TCG CAA CCT CGT GGA AGG CGA CAA CCT     192
Thr Arg Lys Thr Ser Glu Arg Ser Gln Pro Arg Gly Arg Arg Gln Pro
 50                  55                  60

ATC CCC AAG GAT CGC CGG CCC GAG GGC AGG GCC TGG GCT CAA CCT GGG     240
Ile Pro Lys Asp Arg Arg Pro Glu Gly Arg Ala Trp Ala Gln Pro Gly
 65                  70                  75                  80

TAC CCT TGG CCC CTC TAT GGC AAC GAG GGC ATG GGG TGG GCA GGA TGG     288
Tyr Pro Trp Pro Leu Tyr Gly Asn Glu Gly Met Gly Trp Ala Gly Trp
                85                  90                  95

CTC CTG TCA CCC CGT GGC TCC CGG CCT AGT TGG GGC CCC AAT GAC CCC     336
Leu Leu Ser Pro Arg Gly Ser Arg Pro Ser Trp Gly Pro Asn Asp Pro
            100                 105                 110

CGG CGT AGG TCG CGT AAT TTG GGT AAA GTC ATC GAT ACC CTT ACA TGC     384
Arg Arg Arg Ser Arg Asn Leu Gly Lys Val Ile Asp Thr Leu Thr Cys
        115                 120                 125

GGC TTC GCC GAC CTC ATG GGG TAC ATT CCG CTC GTC GGC GCT CCC TTG     432
Gly Phe Ala Asp Leu Met Gly Tyr Ile Pro Leu Val Gly Ala Pro Leu
130                 135                 140

GGG GGC GCT GCC AGG GCC TTG GCG CAT GGC                             462
Gly Gly Ala Ala Arg Ala Leu Ala His Gly
145                 150

(2) INFORMATION FOR SEQ ID NO:2:

(i) SEQUENCE CHARACTERISTICS:
        (A) LENGTH: 154 amino acids
        (B) TYPE: amino acid
        (D) TOPOLOGY: linear (xi) SEQUENCE DESCRIPTION: SEQ ID NO:2:

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
 50                  55                  60

Ile Pro Lys Asp Arg Arg Pro Glu Gly Arg Ala Trp Ala Gln Pro Gly
 65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125
```

```
Gly Phe Ala Asp Leu Met Gly Tyr Ile Pro Leu Val Gly Ala Pro Leu
    130                 135                 140

Gly Gly Ala Ala Arg Ala Leu Ala His Gly
145                 150
```

(2) INFORMATION FOR SEQ ID NO:3:

(i) SEQUENCE CHARACTERISTICS:
        (A) LENGTH: 9 base pairs
        (B) TYPE: nucleic acid
        (C) STRANDEDNESS: double
        (D) TOPOLOGY: linear (xi) SEQUENCE DESCRIPTION: SEQ ID NO:3:

```
CCGTGCACC                                                                      9
```

(2) INFORMATION FOR SEQ ID NO:4:

(i) SEQUENCE CHARACTERISTICS:
        (A) LENGTH: 341 base pairs
        (B) TYPE: nucleic acid
        (C) STRANDEDNESS: double
        (D) TOPOLOGY: linear (xi) SEQUENCE DESCRIPTION: SEQ ID NO:4:

```
GCCAGCCCCC GATTGGGGGC GACACTCCAC CATAGATCAC TCCCCTGTGA GGAACTACTG      60

TCTTCACGCA GAAAGCGTCT AGCCATGGCG TTAGTATGAG TGTCGTGCAG CCTCCAGGAC     120

CCCCCCTCCC GGGAGAGCCA TAGTGGTCTG CGGAACCGGT GAGTACACCG GAATTGCCAG     180

GACGACCGGG TCCTTTCTTG GATCAACCCG CTCAATGCCT GGAGATTTGG GCGTGCCCCC     240

GCGAGACTGC TAGCCGAGTA GTGTTGGGTC GCGAAAGGCC TTGTGGTACT GCCTGATAGG     300

GTGCTTGCGA GTGCCCCGGG AGGTCTCGTA GACCGTGCAC C                         341
```

(2) INFORMATION FOR SEQ ID NO:5:

(i) SEQUENCE CHARACTERISTICS:
        (A) LENGTH: 1200 base pairs
        (B) TYPE: nucleic acid
        (C) STRANDEDNESS: double
        (D) TOPOLOGY: linear (xi) SEQUENCE DESCRIPTION: SEQ ID NO:5:

```
ATG GGA GGT TGG TCT TCC AAA CCT CGA CAA GGC ATG GGG ACG AAT CTT       48
Met Gly Gly Trp Ser Ser Lys Pro Arg Gln Gly Met Gly Thr Asn Leu
  1               5                  10                  15

TCT GTT CCC AAT CCT CTG GGA TTC TTT CCC GAT CAC CAG TTG GAC CCT       96
Ser Val Pro Asn Pro Leu Gly Phe Phe Pro Asp His Gln Leu Asp Pro
                 20                  25                  30

GCG TTC GGA GCC AAC TCA AAC AAT CCA GAT TGG GAC TTC AAC CCC AAC      144
Ala Phe Gly Ala Asn Ser Asn Asn Pro Asp Trp Asp Phe Asn Pro Asn
             35                  40                  45

AAG GAT CAA TGG CCA GAG GAA ATC AAG GTA GGA GCG GGA GAC TTC GGG      192
Lys Asp Gln Trp Pro Glu Glu Ile Lys Val Gly Ala Gly Asp Phe Gly
         50                  55                  60

CCA GGG TTC ACC CCA CCA CAC GGC GGT CTT TTG GGG TGG AGC CCT CAG      240
Pro Gly Phe Thr Pro Pro His Gly Gly Leu Leu Gly Trp Ser Pro Gln
 65                  70                  75                  80

GCT CAG GGC ATA TTG ACA ACA GTG CCA GCA GCG CCT CCT CCT GCC TCC      288
Ala Gln Gly Ile Leu Thr Thr Val Pro Ala Ala Pro Pro Pro Ala Ser
                 85                  90                  95

ACC AAT CGG CAG TCA GGA AGA CAG CCT ACT CCC ATC TCT CCA CCT CTA      336
```

```
         Thr Asn Arg Gln Ser Gly Arg Gln Pro Thr Pro Ile Ser Pro Pro Leu
                         100                 105                 110

AGA GAC AGT CAT CCT CAG GCC ATG CAG TGG AAC TCC ACA ACA TTC CAC            384
Arg Asp Ser His Pro Gln Ala Met Gln Trp Asn Ser Thr Thr Phe His
            115                 120                 125

CAA GCT CTG CTA GAT CCC AGA GTG AGG GGC CTA TAT TTT CCT GCT GGT            432
Gln Ala Leu Leu Asp Pro Arg Val Arg Gly Leu Tyr Phe Pro Ala Gly
        130                 135                 140

GGC TCC AGT TCC GGA ACA GTA AAC CCT GTT CCG ACT ACT GTC TCA CCC            480
Gly Ser Ser Ser Gly Thr Val Asn Pro Val Pro Thr Thr Val Ser Pro
145                 150                 155                 160

ATA TCG TCA ATC TTC TCG AGG ACT GGG GAC CCT GCA CCG AAC ATG GAG            528
Ile Ser Ser Ile Phe Ser Arg Thr Gly Asp Pro Ala Pro Asn Met Glu
                165                 170                 175

AGC ACA ACA TCA GGA TTC CTA GGA CCC CTG CTC GTG TTA CAG GCG GGG            576
Ser Thr Thr Ser Gly Phe Leu Gly Pro Leu Leu Val Leu Gln Ala Gly
            180                 185                 190

TTT TTC TTG TTG ACA AGA ATC CTC ACA ATA CCA CAG AGT CTA GAC TCG            624
Phe Phe Leu Leu Thr Arg Ile Leu Thr Ile Pro Gln Ser Leu Asp Ser
        195                 200                 205

TGG TGG ACT TCT CTC AAT TTT CTA GGG GGA GCA CCC ACG TGT CCT GGC            672
Trp Trp Thr Ser Leu Asn Phe Leu Gly Gly Ala Pro Thr Cys Pro Gly
210                 215                 220

CAA AAT TCG CAG TCC CCA ACC TCC AAT CAC TCA CCA ACC TCT TGT CCT            720
Gln Asn Ser Gln Ser Pro Thr Ser Asn His Ser Pro Thr Ser Cys Pro
225                 230                 235                 240

CCA ATT TGT CCT GGT TAT CGC TGG ATG TGT CTG CGG CGT TTT ATC ATA            768
Pro Ile Cys Pro Gly Tyr Arg Trp Met Cys Leu Arg Arg Phe Ile Ile
                245                 250                 255

TTC CTC TTC ATC CTG CTG CTA TGC CTC ATC TTC TTG TTG GTT CTT CTG            816
Phe Leu Phe Ile Leu Leu Leu Cys Leu Ile Phe Leu Leu Val Leu Leu
            260                 265                 270

GAC TAC CAA GGT ATG TTG CCC GTT TGT CCT CTA CTT CCA GGA ACA TCA            864
Asp Tyr Gln Gly Met Leu Pro Val Cys Pro Leu Leu Pro Gly Thr Ser
        275                 280                 285

ACT ACC AGC ACG GGA CCA TGC AAG ACC TGC ACG ATT CCT GCT CAA GGA            912
Thr Thr Set Thr Gly Pro Cys Lys Thr Cys Thr Ile Pro Ala Gln Gly
290                 295                 300

ACC TCT ATG TTT CCC TCT TGT TGC TGT ACA AAA CCT TCG GAC GGA AAC            960
Thr Ser Met Phe Pro Ser Cys Cys Cys Thr Lys Pro Ser Asp Gly Asn
305                 310                 315                 320

TGC ACT TGT ATT CCC ATC CCA TCA TCC TGG GCT TTC GCA AGA TTC CTA           1008
Cys Thr Cys Ile Pro Ile Pro Ser Ser Trp Ala Phe Ala Arg Phe Leu
                325                 330                 335

TGG GAG TGG GCC TCA GTC CGT TTC TCC TGG CTC AGT TTA CTA GTG CCA           1056
Trp Glu Trp Ala Ser Val Arg Phe Ser Trp Leu Ser Leu Leu Val Pro
            340                 345                 350

TTT GTT CAG TGG TTC GCA GGG CTT TCC CCC ACT GTT TGG CTT TCA GTT           1104
Phe Val Gln Trp Phe Ala Gly Leu Ser Pro Thr Val Trp Leu Ser Val
        355                 360                 365

ATA TGG ATG ATG TGG TAT TGG GGG CCA AGT CTG TAC AAC ATC TTG AGT           1152
Ile Trp Met Met Trp Tyr Trp Gly Pro Ser Leu Tyr Asn Ile Leu Ser
370                 375                 380

CCC TTT TTA CCT CTA TTA CCA ATT TTC TTT TGT CTT TGG GTA TAC ATT           1200
Pro Phe Leu Pro Leu Leu Pro Ile Phe Phe Cys Leu Trp Val Tyr Ile
385                 390                 395                 400

(2) INFORMATION FOR SEQ ID NO:6:

(i) SEQUENCE CHARACTERISTICS:
```

```
        (A) LENGTH: 21 bases
        (B) TYPE: nucleic acid
        (C) STRANDEDNESS: single
        (D) TOPOLOGY: linear (xi) SEQUENCE DESCRIPTION: SEQ ID NO:6:

GGGTCACCAT ATTCTTGGGA A                                              21

(2) INFORMATION FOR SEQ ID NO:7:

(i) SEQUENCE CHARACTERISTICS:
        (A) LENGTH: 21 bases
        (B) TYPE: nucleic acid
        (C) STRANDEDNESS: single
        (D) TOPOLOGY: linear (xi) SEQUENCE DESCRIPTION: SEQ ID NO:7:

GCAGCAAAGC CCAAAAGACC C                                              21

(2) INFORMATION FOR SEQ ID NO:8:

(i) SEQUENCE CHARACTERISTICS:
        (A) LENGTH: 28 bases
        (B) TYPE: nucleic acid
        (C) STRANDEDNESS: single
        (D) TOPOLOGY: linear (xi) SEQUENCE DESCRIPTION: SEQ ID NO:8:

CGGGATCCAT GAGCACGAAT CCTAAACC                                       28

(2) INFORMATION FOR SEQ ID NO:9:

(i) SEQUENCE CHARACTERISTICS:
        (A) LENGTH: 34 bases
        (B) TYPE: nucleic acid
        (C) STRANDEDNESS: single
        (D) TOPOLOGY: linear (xi) SEQUENCE DESCRIPTION: SEQ ID NO:9:

TCTCTAGATT ACTAGCCATG CGCCAAGGCC CTGG                                34

(2) INFORMATION FOR SEQ ID NO:10:

(i) SEQUENCE CHARACTERISTICS:
        (A) LENGTH: 27 bases
        (B) TYPE: nucleic acid
        (C) STRANDEDNESS: single
        (D) TOPOLOGY: linear (xi) SEQUENCE DESCRIPTION: SEQ ID NO:10:

CATGGATCCA ATGTATACCC AAAGACA                                        27

(2) INFORMATION FOR SEQ ID NO:11:

(i) SEQUENCE CHARACTERISTICS:
        (A) LENGTH: 34 bases
        (B) TYPE: nucleic acid
        (C) STRANDEDNESS: single
        (D) TOPOLOGY: linear (xi) SEQUENCE DESCRIPTION: SEQ ID NO:11:

AGACACAAGC TTATGGGAGG TTGGTCTTCC AAAC                                34

(2) INFORMATION FOR SEQ ID NO:12:

(i) SEQUENCE CHARACTERISTICS:
        (A) LENGTH: 31 bases
```

-continued

```
        (B) TYPE: nucleic acid
        (C) STRANDEDNESS: single
        (D) TOPOLOGY: linear (xi) SEQUENCE DESCRIPTION: SEQ ID NO:12:

AGACACAAGC TTGCCGCCAT GCAGTGGAAC T                                    31

(2) INFORMATION FOR SEQ ID NO:13:

(i) SEQUENCE CHARACTERISTICS:
        (A) LENGTH: 9 base pairs
        (B) TYPE: nucleic acid
        (C) STRANDEDNESS: double
        (D) TOPOLOGY: linear (xi) SEQUENCE DESCRIPTION: SEQ ID NO:13:

GCCGCCATG                                                              9
```

CHIMERIC HEPATITIS B/HEPATITIS C VIRUS VACCINE

CROSS REFERENCE TO RELATED APPLICATIONS

This application is a continuation of Ser. No. 08/467,859 filed Jun. 6, 1995, abandoned.

ACKNOWLEDGMENT OF GOVERNMENT RIGHTS

This invention was made with Government support under grants CA-35711 and AA-0186 awarded by the National Institutes of Health. The Government has certain rights in this invention.

FIELD OF THE INVENTION

The present invention relates to recombinant chimeric gene constructs which are useful as anti-hepatitis B virus and/or anti-hepatitis C virus vaccine components in genetic immunization protocols, to methods of protecting individuals against hepatitis B virus and/or hepatitis C virus infection and to methods of treating individuals suffering from hepatitis B virus and/or hepatitis C virus infection.

BACKGROUND OF THE INVENTION

Hepatitis C virus (HCV), the major etiologic agent of transfusion acquired non-A, non-B hepatitis, is responsible for approximately 150,000 new cases of acute viral hepatitis annually in the United States. Approximately half of these infections progress to a chronic infection that can be associated with cirrhosis and/or hepatocellular carcinoma (Alter, et al., *Science*, 1992, 258, 135–140; and Alter, et al., *New Eng. J. Med.*, 1992, 327, 1899–1905). In addition, HCV infection is an independent risk factor for the development of hepatocellular carcinoma as shown by the prevalence of anti-HCV antibodies (Colombo, et al., *Lancet*, 1989, ii, 1006–1008; Saito, et al., *Proc. Natl. Acad. Sci. USA*, 1990, 87, 6547–6549; Simonetti, et al., *An. Int. Med.*, 1992, 116, 97–102; and Tsukuma, et al., *New Eng. J. Med.*, 1993, 328, 1797–1801).

HCV is an enveloped, positive stranded RNA virus, approximately 9,500 nucleotides in length, which has recently been classified as a separate genus within the Flavivirus family (Heinz, F. X., *Arch. Virol. (Suppl.)*, 1992, 4, 163–171). Different isolates show considerable nucleotide sequence diversity leading to the subdivision of HCV genomes into at least eight genotypes (Simmonds, et al., *J. Gen. Virol.*, 1993, 74, 2391–2399). In all genotypes, the viral genome contains a large open reading frame (ORF) that encodes a precursor polyprotein of 3010 to 3033 amino acids of approximately 330 Kd (Choo, et al., *Proc. Natl. Acad. Sci. USA*, 1991, 88, 2451–2455; Inchauspe, et al., *Proc. Natl. Acad. Sci. USA*, 1991, 88, 10292–10296; Kato, et al., *Proc. Natl. Acad. Sci. USA*, 1990, 87, 9524–9528; Okamoto, et al., *J. Gen. Virol.*, 1991, 72, 2697–2704; and Takamizawa, et al., *J. Gen. Virol.*, 1991, 65, 1105–1113).

Individual HCV polypeptides are produced by proteolytic processing of the precursor polypeptide to produce core (C), envelope (E1, E2) and non-structural (NS2–NS5) proteins (Bartenschlager, et al., *J. Gen. Virol.*, 1993, 67, 3835–3844; Grakoui, et al., *J. Gen. Virol.*, 1993, 67, 2832–2843; and Selby, et al., *J. Gen. Virol.*, 1993, 74, 1103–1113). This proteolysis is catalyzed by a combination of both cellular and viral encoded proteases.

In addition to the translated region, the HCV genome also contains both a 5' untranslated region (5' UTR) and a 3' untranslated region (3' UTR). The 5' UTR of 324 to 341 nucleotides represents the most highly conserved sequence among all HCV isolates reported to date (Han, et al., *Proc. Natl. Acad. Sci. USA*, 1991, 88, 1711–1715; and Bukh, et al., *Proc. Natl. Acad. Sci. USA*, 1992, 89, 4942–4946). This 5' UTR has been postulated to contain important regulatory elements for replication and/or translation of HCV RNAs. The 5' UTR also contains several small open reading frames (ORF) but there is presently no evidence to suggest that these ORF sequences are actually translated.

The HCV core gene may be an important target for nucleic acid-based antiviral approaches. The first 191 amino acids of the HCV polyprotein precursor are believed to represent the viral nucleocapsid protein. This protein is comprised of a basic, RNA-binding amino-terminal domain and a highly hydrophobic carboxy-terminal region (Bukh, et al., *Proc. Natl. Acad. Sci. USA*, 1994, 91, 8239–8243; and Santolini, et al., *J. Virol.*, 1994, 68, 3631–3641). The mature 21 kDa core protein is cleaved from the polyprotein precursor by cellular signal peptidase and there is evidence to suggest that the HCV nucleocapsid protein is stably associated with the cytoplasmic surface of the endoplasmic reticulum membrane (Hijikata, et al., *Proc. Natl. Acad. Sci. USA*, 1991, 88, 5547–5551; and Santolini, et al., *J. Virol.*, 1994, 68, 3631–3641). In contrast to the envelope glycoproteins which include a hypervariable region in the amino-terminal region of E2 (Weiner, et al., *Virol.*, 1991, 180, 842–848; and Weiner, et al., *Proc. Natl. Acad. Sci. USA*, 1992, 89, 3468–3472), the core protein is well conserved among the different HCV genotypes and generates a host immune response (Bukh, et al., *Proc. Natl. Acad. Sci. USA*, 1994, 91, 8239–8243; and Houghton, et al., *Hepatology*, 1991, 14, 381–388). Previous studies have shown that the majority of HCV-infected individuals develop antibodies to the HCV core protein early in the course of infection (Chiba, et al., *Proc. Natl. Acad. Sci. USA*, 1991, 88, 4641–4645; Hosein, et al., *Proc. Natl. Acad. Sci. USA*, 1991, 88, 3647–3651; Hsu, et al., *Hepatology*, 1993, 17, 763–771; Katayama, et al., *Hepatology*, 1992, 15, 391–394; Nasoff, et al., *Proc. Natl. Acad. Sci. USA*, 1991, 88, 5462–5466; and Okamoto, et al., *Hepatology*, 1992, 15, 180–186). Furthermore, the nucleocapsid protein represents an important target for the cellular immune response against HCV (Botarelli, et al., *Gastroenterol.*, 1993, 104, 580–587; Koziel, et al., *J. Virol.*, 1993, 67, 7522–7532; and Shirai, et al., *J. Virol.*, 1993, 68, 3334–3342). Finally, there are recent observations to suggest that the HCV core protein may have certain gene regulatory functions as well (Shih, et al., *J. Virol.*, 1993, 67, 5823–5832). The high mutational rate of the viral genome probably occurs during viral replication and through immune selection. This phenomenon may be related to the establishment of persistent viral infection and subsequent disease chronicity (Weiner, et al., *Proc. Natl. Acad. Sci. USA*, 1992, 89, 3468–3472; Kato, et al., *Biochem. Biophys. Res. Comm.*, 1992, 189, 119–127; and Alter, et al., *New Eng. J. Med.*, 1992, 327, 1899–1905).

The cellular immune events involved in liver damage and viral clearance during HCV infection have only partially been defined. In an attempt to examine a potential pathogenic role of liver-infiltrating lymphocytes in patients with chronic HCV infection, Koziel, et al. examined the cytotoxic T lymphocyte (CTL) response of such cells and demonstrated an HLA class I-restricted CD8+ CTL response that was directed against both structural and non-structural regions of HCV polypeptides (Koziel, et al., *J. Virol.*, 1993, 67, 7522–7532; and Koziel, et al., *J. Immunol.*, 1992, 149, 3339–3344). Other investigators have also noted the existence of CTLs in peripheral blood mononuclear cell populations that recognize epitopes on core and the other viral related proteins during chronic HCV infection (Kita, et al., *Hepatol.*, 1993, 18, 1039–1044; and Cerny, et al., *Intl. Symp. Viral Hepatitis Liver Dis.*, 1993, 83 (abstr.)).

Botarelli, et al. (Botarelli, et al., *Gastroenterol.*, 1993, 104, 580–587) and Ferrari, et al. (Ferrari, et al., *Hepatol.*, 1994, 19, 286–295) found HLA class II-restricted CD4+ T cell-mediated proliferative responses to several recombinant proteins derived from different regions of HCV in patients with chronic HCV infection. It is noteworthy that there was a correlation between T cell responses to HCV core protein, and a clinically benign course of the liver disease as well as subsequent eradication of the virus. However, a similar study showed the proliferative response to HCV core protein did not predict a benign clinical course with respect to the severity of the liver disease (Schupper, et al., *Hepatol.*, 1993, 18, 1055–1060). Thus, it is important to clarify the association between active cellular immunity and the clinical course of the viral infection with respect to the type of liver injury and clinical response of HCV infection to IFN therapy. In this regard, studies involving peripheral blood mononuclear cell (PBMC) responses to a recombinant GST-HCV core fusion protein were conducted, and involved evaluating the ability of such cells to produce IFN-γ; correlations were made to different clinical outcomes of HCV infection. It was found that mononuclear cells from 24 (52%) of 46 patients with chronic liver disease responded to the core protein; asymptomatic HCV carriers demonstrated a lower response rate (15%, p<0.05). More important, individuals who had received IFN-A treatment and went into clinical and virologic emission had a higher response rate (75%, p<0.05) to HCV core protein compared to those with ongoing hepatitis who failed therapy (31%). Of 25 patients whose mononuclear cells responded to HCV core protein, 18 had a significant response to one or more peptides; 12 patients reacted to a peptide mixture containing hydrophilic sequences. The core peptide amino acid sequence 140–160 was recognized by 9 patients. Interestingly, 7 of 8 patients bearing HLA DR4 and w53 haplotypes recognized the peptide sequence 141–160. Thus, the mononuclear cell response appeared to be HLA DR restricted and the responding cells were identified as CD4+ T cells. This study demonstrates the presence of immunodominant T cell epitopes within the HCV core protein in association with HLA DR phenotypes in patients with HCV associated liver disease.

Hepatitis B virus (HBV) is a major human pathogen for which there is no effective therapy. It is estimated that more than 300 million people are chronically infected with this virus worldwide. Exposure to HBV may result in acute or chronic hepatitis, liver cirrhosis and the development of hepatocellular carcinoma. The clinical consequences of this serious infection are of particular concern in the developing world where HBV infection is one of the leading causes of mortality and is also a major cause of acute and chronic liver disease in the United States and Europe as well. HBV is the prototype member of the hepadnavirus family, a group of closely related viruses (Ganem, et al., *Annu. Rev. Biochem.*, 1987, 56, 651–693) that including, among others, the duck hepatitis B virus (DHBV) and the woodchuck hepatitis virus (WHV). Experimentally infected ducks or woodchucks faithfully reproduce many of the features of human disease such as acute and chronic infection and, in the case of chronically infected woodchucks, the development of hepatocellular carcinoma (Schodel, et al., "The Biology of Avian Hepatitis B viruses", In Molecular Biology of the Hepatitis B Virus, 1991, Vol.3, CRC Press, Boca Raton, Fla., pp.53–80; Korba, et al., *J. Virol.*, 1989, 63, 1360–1370; and Korba, et al., *Hepatology*, 1989, 9, 461–470). Although viral replicative intermediates have been found in other tissues, the liver is the target organ and hepatocyte injury is associated with persistent viral infection. HBV per se appears not to be a cytopathic virus. It is likely, therefore, that the host immune response produced against viral epitopes produces the liver injury and treatment strategies designed to reduce viral replication in the liver may have beneficial clinical effects.

The HBV genome encodes for 4 open reading frames (ORF) that includes: 1) the S gene encoding for the envelope protein with 2 in-frame pre-S1 and pre-S2 polypeptides; 2) the polymerase ORF encoding for a reverse transcriptase protein that is responsible for reverse transcription of a 3.6 kb pregenomic RNA into DNA; 3) the core gene encoding for a protein that is assembled to complete the viral nucleocapsid; and 4) the HBx ORF encodes for a protein of unknown function. The pol gene encompasses 800% of the genome and overlaps with the other three ORFs. The core gene is preceded by an in-frame sequence that encodes for a signal peptide and following proteolytic cleavage gives rise to an antigenically distinct protein called the HBeAg. The HBx protein was found not to be essential for the viral life cycle in vitro (Blum, et al., *J. Virol.*, 1992, 66, 123–127), but it appears to be necessary for the establishment of productive infection in vivo (Chen, et al., *J. Virol.*, 1993, 67, 1218–1226). HBx can function as a transcriptional transactivator on a variety of cellular and viral genes and suggests that is may contribute to HCC development (Schek, et al., "The Hepadnaviral X Protein", In Molecular Biology of the Hepatitis B Virus, 1991, Vol.9, CRC Press, Boca Raton, Fla., pp.181–192).

Direct injection of DNA into animals is a promising method for delivering specific antigens for immunization (Barry, et al., *Bio Techniques*, 1994, 16, 616–619; Davis, et al., *Hum. Mol. Genet.*, 1993, 11, 1847–1851; Tang, et al., *Nature*, 1992, 356, 152–154; Wang, et al., *J. Virol.*, 1993, 67, 3338–3344; and Wolff, et al., *Science*, 1990, 247, 1465–1468). This approach has been successfully used to generate protective immunity against influenza virus in mice and chickens, against bovine herpes virus 1 in mice and cattle and against rabies virus in mice (Cox, et al., *J. Virol.*, 1993, 67, 5664–5667; Fynan, et al., *DNA and Cell Biol.*, 1993, 12, 785–789; Ulmer, et al., *Science*, 1993, 259, 1745–1749; and Xiang, et al., *Virol.*, 1994, 199, 132–140). In most cases, strong, yet highly variable, antibody and cytotoxic T-cell responses were associated with control of infection. Indeed, the potential to generate long-lasting memory CTLs without using a liver vector makes this approach particularly attractive compared with those involving killed-virus vaccines and generating a CTL response that not only protects against acute infection but also may have benefits in eradicating persistent viral infection (Wolff, et al., *Science*, 1990, 247, 1465–1468; Wolff, et al., *Hum. Mol. Genet.*, 1992, 1, 363–369; Manthorpe, et al., *Human Gene Therapy*, 1993, 4, 419–431; Ulmer, et al., *Science*, 1993, 259, 1745–1749; Yankauckas, et al., *DNA and Cell Biol.*, 1993, 12, 777–783; Montgomery, et al., *DNA and Cell Biol.*, 1993, 12, 777–783; Fynan, et al., *DNA and Cell Biol.*, 1993, 12, 785–789; Wang, et al., *Proc. Natl. Acad. Sci. USA*, 1993, 90, 4156–4160; Wang, et al., *DNA and Cell Biol.*, 1993, 12, 799–805; Xiang, et al., *Virol.*, 1994, 199, 132–140; and Davis, et al., *Hum. Mol. Genet.*, 1993, 11, 1847–1851) of which HCV and HBV are important human diseases of world wide significance.

Presently, there is no universal, highly effective therapy of chronic HBV and/or HCV infection. Development of a vaccine strategy for HBV and/or HCV is complicated not only by the significant heterogeneity among HBV and HCV isolates, but also by the mixture of heterogeneous genomes within an isolate (Martell, et al., *J. Virol.*, 1992, 66, 3225). In addition, the virus contains a highly variable envelope region.

Vaccination and immunization generally refer to the introduction of a non-virulent agent against which an individual's immune system can initiate an immune response which will then be available to defend against challenge by a pathogen. The immune system identifies invading "foreign" compositions and agents primarily by identifying proteins and other large molecules which are not normally present in the individual. The foreign protein represents a target against which the immune response is made.

PCT patent application PCT/US90/01348 discloses sequence information of clones of the HCV genome, amino acid sequences of HCV viral proteins and methods of making and using such compositions including anti-HCV vaccines comprising HCV proteins and peptides derived therefrom.

U.S. Ser. No. 08/008,342 filed Jan. 26, 1993, U.S. Ser. No. 08/029,336 filed Mar. 11, 1993, U.S. Ser. No. 08/125,012 filed Sep. 21, 1993, PCT patent application Ser. No. PCT/US94/00899 filed Jan. 26, 1994, and U.S. Ser. No. 08/221,579 filed Apr. 1, 1994 each contains descriptions of genetic immunization protocols. Vaccines against HCV are disclosed in each.

U.S. Ser. No. 08/318,248 filed Oct. 5, 1994, which is incorporated herein by reference, discloses genetic constructs comprising nucleotide sequences encoding HCV core protein which are useful as a vaccine. The HCV core DNA-based vaccine expresses high levels of core antigen in vitro and induces a strong immune response in vivo.

There remains a need for vaccines useful to protect individuals against hepatitis B virus and/or hepatitis C virus infection. There remains a need for methods of protecting individuals against hepatitis B virus and/or hepatitis C virus infection.

SUMMARY OF THE INVENTION

The present invention relates to recombinant nucleic acid molecules comprising a nucleotide coding sequence that encodes a fusion protein. The fusion protein comprises hepatitis B virus S gene product linked to amino acids 1–69 of hepatitis C virus core protein.

The present invention relates to pharmaceutical compositions comprising a recombinant nucleic acid molecule that comprises a nucleotide coding sequence that encodes a fusion protein. The fusion protein comprises hepatitis B virus S gene product linked to amino acids 1–69 of hepatitis C virus core protein. The nucleotide coding sequence that encodes the fusion protein is operably linked to regulatory elements functional in human cells. The pharmaceutical composition additionally comprises a pharmaceutically acceptable carrier or diluent.

The present invention relates to methods of immunizing an individual susceptible to or infected by hepatitis C virus and/or hepatitis B virus comprising the step of administering to such an individual, a pharmaceutical composition comprising a recombinant nucleic acid molecule which comprises a nucleotide coding sequence that encodes a fusion protein. The fusion protein comprises hepatitis B virus S gene product linked to amino acids 1–69 of hepatitis C virus core protein. The nucleotide coding sequence that encodes the fusion protein is operably linked to regulatory elements functional in human cells. The pharmaceutical composition additionally comprises a pharmaceutically acceptable carrier or diluent. The individual is administered an amount effective to induce a protective or therapeutic immune response against hepatitis B virus and/or hepatitis C virus infection.

BRIEF DESCRIPTION OF THE FIGURE

FIG. 1 shows a schematic of the plurality of constructs comprising the HCV core gene, the HBV S gene, the HBV pre S1 gene, and the HBV pre S2 gene.

FIG. 2 shows a diagram of an expression vector into which coding sequences encoding a chimeric HCV/HBV fusion protein can be inserted.

FIG. 3 depicts methods for constructing the HBV/HCV fusion constructs.

DETAILED DESCRIPTION OF THE INVENTION

According to the present invention, compositions and methods are provided which prophylactically and/or therapeutically immunize an individual against HBV and/or HCV infection. Recombinant nucleic acid molecules comprising a nucleotide coding sequence that encodes a fusion protein that comprises HBV S gene product linked to amino acids 1–69 of HCV core protein are administered to the individual. The fusion protein encoded by the gene construct is expressed by the individual's cells and serves as an immunogenic target against which an anti-HBV and/or anti-HCV immune responses are elicited. The resulting immune responses are broad based; in addition to a humoral immune response, both arms of the cellular immune response are elicited. The methods of the present invention are useful for conferring prophylactic and therapeutic immunity. Thus, a method of immunizing includes both methods of protecting an individual from HBV and/or HCV challenge as well as methods of treating an individual suffering from HBV and/or HCV infection.

It has been shown that many proteins previously known to induce a humoral and cellular immune responses following DNA immunization have either been native cell surface proteins or secreted proteins, such as, for example, influenza NP, HBsAg, and rabies virus glycoproteins. Although HCV core DNA-based vaccine expresses high levels of core antigen in vitro and induces an immune response in vivo, it is likely that the HCV core protein remains anchored in the cytoplasm and is not expressed on the surface of the cell or secreted from the cell. Therefore, the immune response may be increased by providing for cell surface expression and/or secretion of the protein. Accordingly, the nucleotide coding sequence encoding HCV core protein was linked to regions of the nucleotide coding sequence encoding HBV surface antigen, as shown in FIG. 1. Thus, the chimeric HBV/HCV fusion protein can elicit an immune response to HBV and/or HCV.

As used herein the term "HCV core protein" is meant to refer to HCV core protein having the amino acid sequence set forth in SEQ ID NO:1 and SEQ ID NO:2, which comprises 154 amino acids. The HCV core protein normally has 191 amino acids, but for the purposes of the present invention, the C-terminal 37 amino acids (amino acids 155–191) have been deleted to enhance the ability of the fusion protein to be secreted. The C-terminal twenty amino acids of the HCV core protein are postulated to contain the binding sites to the endoplasmic reticulum, resulting in the retention of the core protein inside the cell cytoplasm. In addition, the term HCV core protein is meant to refer to corresponding HCV core proteins from additional HCV isolates which may vary. Those having ordinary skill in the art can readily identify the HCV core protein from additional HCV isolates. Nucleotide and amino acid sequences for HCV core protein have been disclosed in U.S. Ser. No. 08/318,248 filed Oct. 5, 1994, abandoned, which is incorporated herein by reference. It is to be understood that nucleotide substitutions in the codon may be acceptable when the same amino acid is encoded. In addition, it is also to be understood that nucleotide changes may be acceptable wherein a conservative amino acid substitution results from the nucleotide substitution.

As used herein, the term "gene construct" is meant to refer to a recombinant nucleic acid molecule comprising a nucleotide coding sequence that encodes a fusion protein that comprises at least the N-terminal 69 amino acids of the HCV core protein, and the entire HBV S gene product, as well as initiation and termination signals operably linked to regulatory elements including a promoter and polyadenylation signal capable of directing expression in the cells of the vaccinated individual. In some embodiments, the gene construct further comprises an enhancer, Kozak sequence (GCCGCCATG SEQ ID NO:13), and at least a fragment of the HCV 5' UTR.

As used herein, the term "genetic vaccine" refers to a pharmaceutical preparation that comprises a gene construct. Genetic vaccines include pharmaceutical preparations useful to invoke a prophylactic and/or therapeutic immune response to HCV and or HBV.

According to the present invention, gene constructs are introduced into the cells of an individual where it is expressed, thus producing a HCV core/HBV surface antigen fusion protein. The regulatory elements of the gene constructs of the invention are capable of directing expression in human cells. The regulatory elements include a promoter and a polyadenylation signal. In addition, other elements, such as an enhancer and a Kozak sequence, may also be included in the gene construct.

When taken up by a cell, the gene constructs of the invention may remain present in the cell as a functioning extrachromosomal molecule or it may integrate into the cell's chromosomal DNA. DNA may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the gene construct as a linear minichromosome including a centromere, telomeres and an origin of replication.

According to the present invention, the gene construct comprises recombinant nucleic acid molecules comprising a nucleotide coding sequence that encodes a fusion protein that comprises regions of the HBV S gene product linked to HCV core protein.

In some preferred embodiments, the recombinant nucleic acid molecule comprises a nucleotide coding sequence that encodes a fusion protein that comprises the entire HBV S gene product linked to amino acids 1–69 of HCV core protein. The nucleotides encoding the C-terminal amino acids of HBV S gene product are linked to the nucleotides encoding the N-terminal amino acids of HCV core protein.

In some preferred embodiments, the recombinant nucleic acid molecule comprises a nucleotide coding sequence that encodes a fusion protein that comprises the entire HBV S gene product linked to amino acids 1-70 to 1-154 of HCV core protein. The HCV core protein may comprise amino acids 1-70, 1-71, 1-72, 1-73, 1-74 . . . 1-150, 1-151, 1-152, 1-153, or 1-154. As used herein "1-70 to 1-154" and "1-70, 1-71, 1-72, 1-73, 1-74 . . . 1-150, 1-151, 1-152, 1-153, or 1-154" are used interchangeably and are meant to describe each of the 83 amino acids sequences of fragments of HCV core protein that include 1–69 plus each additional C terminal residue up to 154. The nucleotides encoding the C-terminal amino acids of HBV S gene product are linked to the nucleotides encoding the N-terminal amino acids of HCV core protein.

In some preferred embodiments, the recombinant nucleic acid molecule comprises a nucleotide coding sequence that encodes a fusion protein that comprises a fragment of HBV pre S2 gene product linked to the entire HBV S gene product linked to amino acids 1–69 of HCV core protein. A fragment of HBV pre S2 gene product may include the C-terminal amino acid, or the C-terminal 2 amino acids, or the C-terminal 3 amino acids, or the C-terminal 4 amino acids . . . or the entire HBV pre S2 gene product. As used herein, "a fragment of HBV pre S2 gene product may include the C-terminal amino acid, or the C-terminal 2 amino acids, or the C-terminal 3 amino acids, or the C-terminal 4 amino acids . . . or the entire HBV pre S2 gene product" is meant to describe amino acid sequences that include fragments of the HBV pre S2 starting with the fragment that includes only the C terminal residue to fragments that include additional residues immediately N terminal to the C terminal residue, i.e. the last C terminal residue, the last two C terminal residues, the last three C terminal residues and so on until the entire pre S2 protein is present. The nucleotides encoding the C-terminal amino acids of the HBV pre S2 gene product are linked to the nucleotides encoding the N-terminal amino acids of the HBV S gene product. The nucleotides encoding the C-terminal amino acids of the HBV S gene product are in turn linked to the nucleotides encoding the N-terminal amino acids of HCV core protein.

In some preferred embodiments, the recombinant nucleic acid molecule comprises a nucleotide coding sequence that encodes a fusion protein that comprises a fragment of HBV pre S2 gene product linked to the entire HBV S gene product linked to amino acids 1-70 to 1-154 of HCV core protein. A fragment of HBV pre S2 gene product may include the C-terminal amino acid, or the C-terminal 2 amino acids, or the C-terminal 3 amino acids, or the C-terminal 4 amino acids . . . or the entire HBV pre S2 gene product. The HCV core protein may comprise amino acids 1-70, 1-71, 1-72, 1-73, 1-74 . . . 1-150, 1-151, 1-152, 1-153, or 1-154. The nucleotides encoding the C-terminal amino acids of the HBV pre S2 gene product are linked to the nucleotides encoding the N-terminal amino acids of the HBV S gene product. The nucleotides encoding the C-terminal amino acids of the HBV S gene product are in turn linked to the nucleotides encoding the N-terminal amino acids of HCV core protein.

In some preferred embodiments, the recombinant nucleic acid molecule comprises a nucleotide coding sequence that encodes a fusion protein that comprises a fragment of HBV pre S1 gene product linked to a fragment of HBV pre S2 gene product linked to the entire HBV S gene product linked to amino acids 1–69 of HCV core protein. A fragment of HBV pre S1 gene product may include the C-terminal amino acid, or the C-terminal 2 amino acids, or the C-terminal 3 amino acids, or the C-terminal 4 amino acids . . . or the entire HBV pre S1 gene product. As used herein, "a fragment of HBV pre S1 gene product may include the C-terminal amino acid, or the C-terminal 2 amino acids, or the C-terminal 3 amino acids, or the C-terminal 4 amino acids . . . or the entire HBV pre S1 gene product" is meant to describe amino acid sequences that include fragments of the HBV pre S1 starting with the fragment that includes only the C terminal residue to fragments that include additional residues immediately N terminal to the C terminal residue, i.e. the last C terminal residue, the last two C terminal residues, the last three C terminal residues and so on until the entire pre S1 protein is present. A fragment of HBV pre S2 gene product may include the C-terminal amino acid, or the C-terminal 2 amino acids, or the C-terminal 3 amino acids, or the C-terminal 4 amino acids . . . or the entire HBV pre S2 gene product. The nucleotides encoding the C-terminal amino acids of HBV pre S1 gene product are linked to the nucleotides encoding the N-terminal amino acids of HBV pre S2 gene product. The nucleotides encoding the C-terminal amino acids of the HBV pre S2 gene product are in turn linked to the nucleotides encoding the N-terminal amino acids of HBV S gene product. The nucleotides encoding the C-terminal amino acids of HBV S gene product are in turn linked to the nucleotides encoding the N-terminal amino acids of HCV core protein.

In some preferred embodiments, the recombinant nucleic acid molecule comprises a nucleotide coding sequence that encodes a fusion protein that comprises a fragment of HBV pre S1 gene product linked to a fragment of HBV pre S2 gene product linked to HBV S gene product linked to amino acids 1-70 to 1-154 of HCV core protein. The HCV core protein may comprise amino acids 1-70, 1-71, 1-72, 1-73, 1-74 . . . 1-150, 1-151, 1-152, 1-153, or 1-154. A fragment of HBV pre S1 gene product may include the C-terminal amino acid, or the C-terminal 2 amino acids, or the C-terminal 3 amino acids, or the C-terminal 4 amino acids . . . or the entire HBV pre S1 gene product. A fragment of HBV pre S2 gene product may include the C-terminal amino acid, or the C-terminal 2 amino acids, or the C-terminal 3 amino acids, or the C-terminal 4 amino acids . . . or the entire HBV pre S2 gene product. The nucleotides encoding the C-terminal amino acids of HBV pre S1 gene product are linked to the nucleotides encoding the N-terminal amino acids of HBV pre S2 gene product. The nucleotides encoding the C-terminal amino acids of HBV pre S2 gene product are in turn linked to the nucleotides encoding the N-terminal amino acids of HBV S gene product. The nucleotides encoding the C-terminal amino acids of HBV S gene product are in turn linked to the nucleotides encoding the N-terminal amino acids of HCV core protein.

It is contemplated that the nucleotide coding sequences may be linked to one another with or without nucleotide spacers or linkers, such that the downstream nucleotide coding sequence remains in-frame. Thus, the nucleotide coding sequences may be linked directly, that is, without any nucleotide spacers. Alternatively, a spacer comprising from about 3 to about 60 nucleotides may be inserted between adjacent nucleotide coding sequences. For example, a nucleotide spacer may be inserted between the nucleotide coding sequences for HBV S gene and HCV core gene, between HBV pre S2 gene HBV S gene, and HBV pre S1 gene and HBV pre S2 gene. The spacer or linker may comprise restriction endonuclease sites for cloning purposes.

It is also contemplated that the recombinant nucleic acid molecule comprising a nucleotide coding sequence that encodes a fusion protein that may comprise less than the entire HBV S gene product linked to amino acids 1–69 of HCV core protein, without substantially altering the effectiveness of the vaccine. It is also contemplated that nucleotide substitutions may be made throughout the nucleotide coding sequence without affecting the amino acid sequence of the fusion protein. It is also contemplated that conservative amino acid substitutions may be made throughout the fusion protein without substantially reducing the immunogenic activity of the fusion protein.

In some preferred embodiments, the gene construct includes at least a fragment of the HCV 5' UTR including the last 9 nucleotides of the HCV 5' UTR. As used herein, the term "the last 9 nucleotides of the HCV 5' UTR" is meant to refer to the 9 most 3' nucleotides of the 5' UTR. That is, the 9 nucleotides of the 5' UTR that immediately precede the coding sequence. The last 9 nucleotides of the HCV 5' UTR of a preferred embodiment is shown as SEQ ID NO:3.

In some embodiments, the fragment of the 5' UTR that includes the last 9 nucleotides of the HCV 5' UTR comprises the last 25 nucleotides of the HCV 5' UTR. In some embodiments, the fragment of the 5' UTR that includes the last 9 nucleotides of the HCV 5' UTR comprises the last 50 nucleotides of the HCV 5' UTR. In some embodiments, the fragment of the 5' UTR that includes the last 9 nucleotides of the HCV 5' UTR comprises the last 75 nucleotides of the HCV 5' UTR. In some embodiments, the fragment of the 5' UTR that includes the last 9 nucleotides of the HCV 5' UTR comprises the last 100 nucleotides of the HCV 5' UTR. In some embodiments, the fragment of the 5' UTR that includes the last 9 nucleotides of the HCV 5' UTR comprises the last 150 nucleotides of the HCV 5' UTR. In some embodiments, the fragment of the 5' UTR that includes the last 9 nucleotides of the HCV 5' UTR comprises the last 200 nucleotides of the HCV 5' UTR. In some embodiments, the fragment of the 5' UTR that includes the last 9 nucleotides of the HCV 5' UTR comprises the last 250 nucleotides of the HCV 5' UTR. In some embodiments, the fragment of the 5' UTR that includes the last 9 nucleotides of the HCV 5' UTR comprises the last 300 nucleotides of the HCV 5' UTR.

In some preferred embodiments, the gene construct includes the entire HCV 5' UTR. In some preferred embodiments, the gene construct includes the 9 most 3' nucleotides of the HCV 5' UTR. The entire HCV 5' UTR of a preferred embodiment is shown as SEQ ID NO:4.

The regulatory elements necessary for gene expression of a DNA molecule include: a promoter, an initiation codon, a stop codon, and a polyadenylation signal. In addition, enhancers are often required for gene expression. It is necessary that these elements be operably linked to the sequence that encodes the fusion protein and that the regulatory elements are operable in the individual to whom they are administered.

Initiation codons and stop codon are generally considered to be part of a nucleotide sequence that encodes the fusion protein.

Promoters and polyadenylation signals used must be functional within the cells of the individual. In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for gene expression, other elements may also be included in a gene construct. Such additional elements include enhancers. The enhancer may be selected from the group including but not limited to: human Actin, human Myosin, human Hemoglobin, human muscle creatine and viral enhancers such as those from CMV, RSV and EBV.

Gene constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

Figure 2:
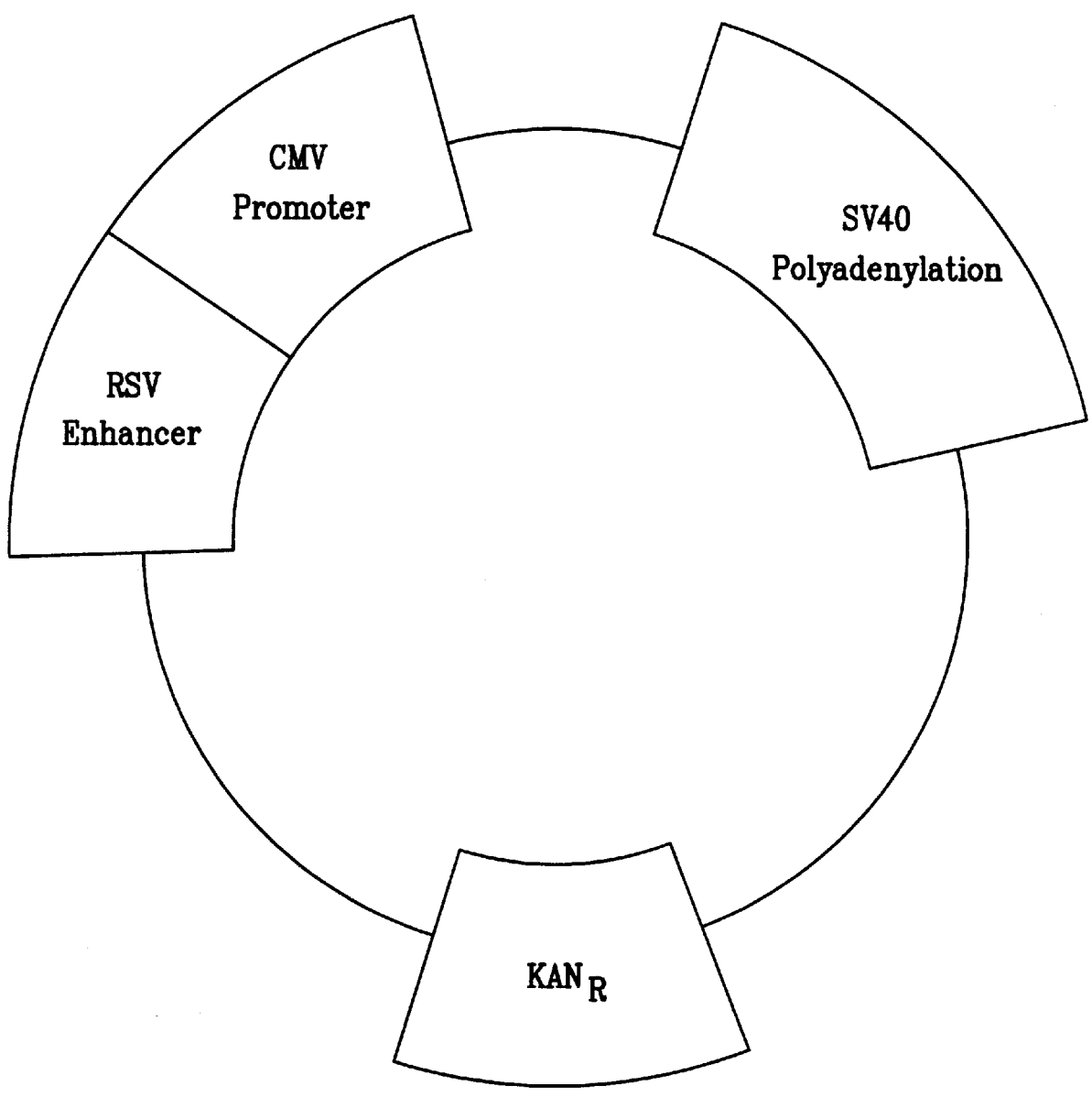

In some preferred embodiments, the gene construct used is selected from the vectors described in FIG. 2. In some embodiments, nucleotide coding sequence encoding the fusion protein is inserted into backbone A.

In expression vectors of the invention, nucleotide coding sequence encoding the fusion protein is under the regulatory control of the CMV immediate early promoter and the SV40 minor polyadenylation signal. Constructs may optionally contain the SV40 origin of replication.

Routes of administration include, but are not limited to, intramuscular, intraperitoneal, intradermal, subcutaneous, intravenous, intraarterially, intraoccularly and oral as well as transdermally or by inhalation or suppository. Preferred routes of administration include intramuscular, intraperitoneal, intradermal and subcutaneous injection. Delivery of gene constructs which encode chimeric HBV/HCV protein can confer mucosal immunity in individuals immunized by a mode of administration in which the material is presented in tissues associated with mucosal immunity. Thus, in some examples, the gene construct is delivered by administration in the buccal cavity within the mouth of an individual.

Gene constructs may be administered by means including, but not limited to, traditional syringes, needleless injection devices, or "microprojectile bombardment gene guns". Alternatively, the genetic vaccine may be introduced by various means into cells that are removed from the individual. Such means include, for example, ex vivo transfection, electroporation, microinjection and microprojectile bombardment. After the gene construct is taken up by the cells, they are reimplanted into the individual. It is contemplated that otherwise non-immunogenic cells that have gene constructs incorporated therein can be implanted into the individual even if the vaccinated cells were originally taken from another individual.

According to some embodiments of the present invention, the gene construct is administered to an individual using a needleless injection device. According to some embodiments of the present invention, the gene construct is simultaneously administered to an individual intradermally, subcutaneously and intramuscularly using a needleless injection device. Needleless injection devices are well known and widely available. One having ordinary skill in the art can, following the teachings herein, use needleless injection devices to deliver genetic material to cells of an individual. Needleless injection devices are well suited to deliver genetic material to all tissue. They are particularly useful to deliver genetic material to skin and muscle cells. In some embodiments, a needleless injection device may be used to propel a liquid that contains DNA molecules toward the surface of the individual's skin. The liquid is propelled at a sufficient velocity such that upon impact with the skin the liquid penetrates the surface of the skin, permeates the skin and muscle tissue therebeneath. Thus, the genetic material is simultaneously administered intradermally, subcutaneously and intramuscularly. In some embodiments, a needleless injection device may be used to deliver genetic material to tissue of other organs in order to introduce a nucleic acid molecule to cells of that organ.

The genetic vaccines according to the present invention comprise about 1 nanogram to about 1000 micrograms of DNA. In some preferred embodiments, the vaccines contain about 10 nanograms to about 800 micrograms of DNA. In some preferred embodiments, the vaccines contain about 0.1 to about 500 micrograms of DNA. In some preferred embodiments, the vaccines contain about 1 to about 350 micrograms of DNA. In some preferred embodiments, the vaccines contain about 25 to about 250 micrograms of DNA. In some preferred embodiments, the vaccines contain about 100 micrograms DNA.

The genetic vaccines according to the present invention are formulated according to the mode of administration to be used. One having ordinary skill in the art can readily formulate a pharmaceutical composition that comprises a gene construct. In some cases, an isotonic formulation is used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free.

The gene constructs of the invention may be formulated with or administered in conjunction with agents that increase uptake and/or expression of the gene construct by the cells relative to uptake and/or expression of the gene construct by the cells that occurs when the identical genetic vaccine is administered in the absence of such agents. Such agents and the protocols for administering them in conjunction with gene constructs are described in U.S. Ser. No. 08/008,342 filed Jan. 26, 1993, abandoned, U.S. Ser. No. 08/029,336 filed Mar. 11, 1993, abandoned, U.S. Pat. No. 5,593,972, filed Jan. 4, 1997, PCT patent application Ser. No. PCT/US94/00899 filed Jan. 26, 1994, and U.S. Pat. No. 5,739,118, filed Apr. 14, 1994, which are each incorporated herein by reference. Examples of such agents include: $CaPO_4$, DEAE dextran, anionic lipids; extracellular matrix-active enzymes; saponins; lectins; estrogenic compounds and steroidal hormones; hydroxylated lower alkyls; dimethyl sulfoxide (DMSO); urea; and benzoic acid esters anilides, amidines, urethanes and the hydrochloride salts thereof such as those of the family of local anesthetics. In addition, the gene constructs are encapsulated within/administered in conjunction with lipids/polycationic complexes.

EXAMPLES

Example 1

Design and Construction of HBV/HCV Expression Plasmids

A large S HB clone containing the entire pre S1, pre S2, and S sequences (adr-1) was established. The nucleotide and amino acid sequences of the pre S1/pre S2/S gene is depicted in SEQ ID NO:5. Briefly, 100 μl of serum obtained from a patient with HBV related chronic hepatitis was incubated at 70° C. for 3 hours in a mixture of proteinase K (100 μg/ml), 0.5% SDS, 5 mM EDTA, and 10 mm Tris-HCl, pH 8.0. The solution was extracted with phenol-chloroform and the DNA precipitated with ethanol. A PCR reaction was conducted in a 100 μl mixture containing 10 μl of serum DNA sample, 2.5 U Taq polymerase (Perkin-Elmer Cetus, Norwalk, Conn), 50 μM of each dNTP, and 0.4 μM of primer HBs-3 5'-GGGTCACCATATTCTTGGGAA-3' (SEQ ID NO:6) and HBs-1 5'-GCAGCAAAGCCCAAAAGACCC-3' (SEQ ID NO:7). The reaction mixture was cycled 35 times. Amplified DNA was cloned into pCR™ vector using TA cloning kit (Invitrogen). The HCV clone (TH, genotype II) was also established from a patient with chronic hepatitis C infection as described by Wakita, et al., *J. Biol. Chem.*, 1994, 269, 1405–1410, which is disclosed herein by reference.

Figure 3:
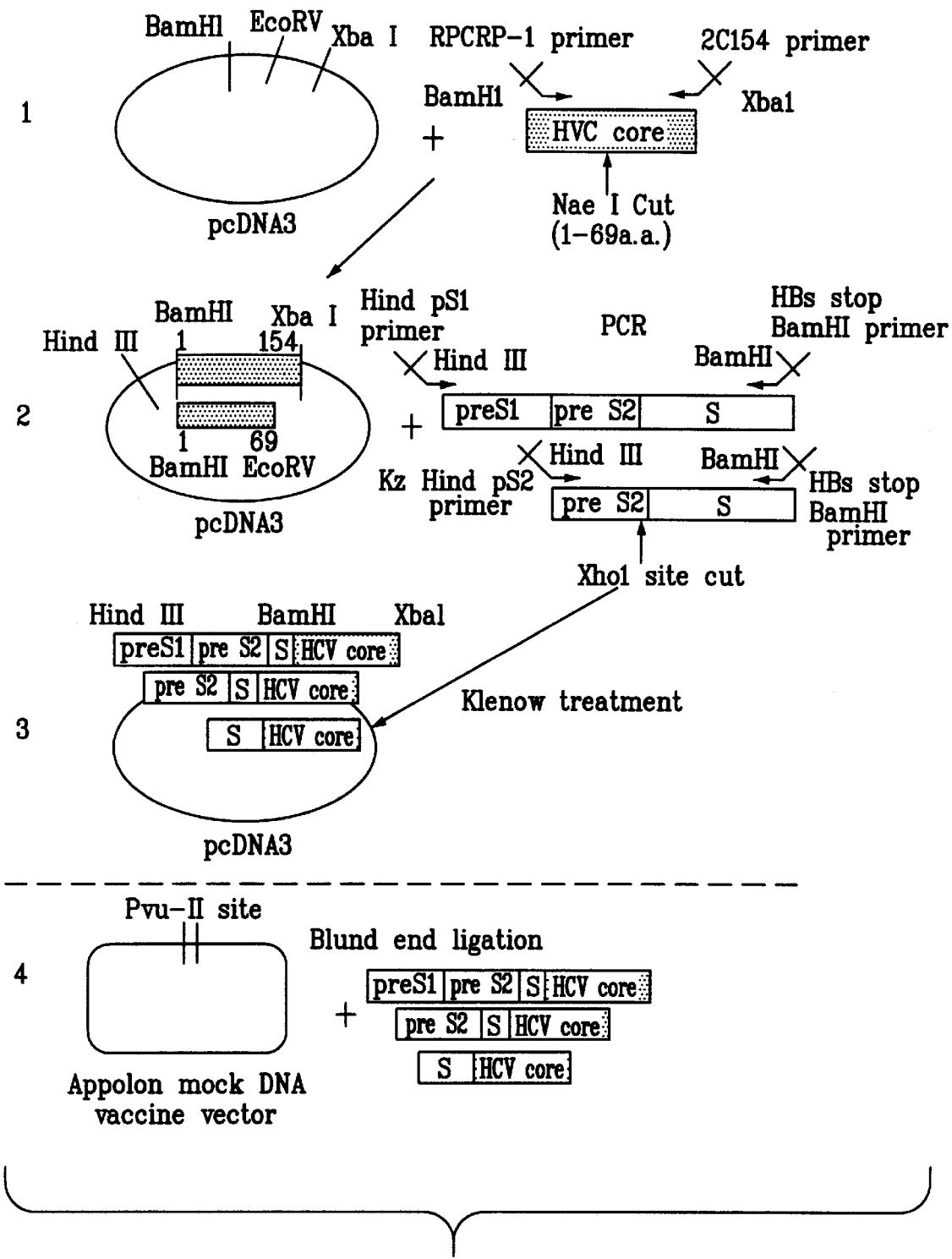

FIG. 3 depicts preferred methods used to prepare the HCV/HBV fusion constructs. The first step required PCR amplification of the HCV core gene. In brief, 10 μg of TH-DNA was amplified by RPCRP-1 primer 5'-CGGGATCCATGAGCACGAATCCTAAACC-3' (SEQ ID NO:8) and 2C154XBA-R 5'-TCTCTAGATTACTAGCCATGCGCCAAGGCCCTGG-3' (SEQ ID NO:9) primer. The PCR product was digested with BamHI and XbaI, and ligated into the pcDNA3 vector (Invitrogen). The final 20 amino acids of the HCV core protein binds tightly to ER membrane. Considering this information, with respect to fusion protein secretion, the final 37 amino acids of the HCV core protein (amino acids 155 to 191) were deleted. Another plasmid encoding a shortened HCV core gene (HCV core amino acids 1 to 69) was also produced because it was possible that the fusion proteins containing HCV core amino acids 1 to 154 will be too long to be secreted. To make the shortened HCV construct, amplified DNA was digested with BamHI and NaeI and ligated into BamHI site-EcoRl site in the pcDNA3 vector.

Finally, the PCR of the HBs product was produced between the HBs stop BamHI primer 5'-CATGGATCCAATGTATACCCAAAGACA-3' (SEQ ID NO:10) and Hind pS1 primer 5'-AGACACAAGCTTATGGGAGGTTGGTCTTCCAAAC-3' (SEQ ID NO:11) or Kz Hind pS2 primer 5'-AGACACAAGCTTGCCGCCATGCAGTGGAACT-3' (SEQ ID NO:12). Amplified DNA was digested with BamHI and HindIII, and ligated into the BamHI site-HindIII site of the pcDNA3 vector that included the HCV core gene. The gene encoding the small S was produced by digestion of middle S (pre S2-S) PCR product by Xho-I followed by Klenow treatment. In the upstream sequence of the pre-S2-S-HCV fusion constructs, a Kozak sequence (GCCGCCATG SEQ ID NO:13) was included in the Kz Hind pS2 primer and this was added to the preS2-S-HCV construct since the pre-S2-S-HCV construct without the Kozac sequence was frequently translated from the ATG codon of HBs gene (small S) and not from the ATG codon of pre S2 gene. As shown in FIG. 1, six fusion constructs were prepared. Complete sequence analysis of all constructs was performed and no PCR-induced mutations were found. Finally, these six HB-HCV inserts were ligated to Pvu-II site of vaccine expression vector.

One skilled in the art having the DNA sequences encoding the HCV core protein, the pre S1 protein, the pre S2 protein, and the S protein can design primers for preparing any of the chimeric gene constructs of the present invention. In addition, nucleotide base substitutions may be made without affecting the binding of the primers. Moreover, the primers may be prepared with endonuclease restriction sites for cloning and ligating purposes, as known to those skilled in the art. Thus, one skilled in the art can prepare any of the gene constructs of the present invention by designing the appropriate primers and performing PCR amplification. The PCR products are ligated into an expression vector.

Plasmids comprising the nucleotide coding sequence for the HBV/HCV fusion proteins described above each contain the nucleotide coding region for the fusion protein placed under the transcriptional control of the CMV promoter and the RSV enhancer element.

Plasmid backbone A is 3969 base pairs in length. It contains a PBR origin of replication for replicating in *E. coli*. It also contains a kanamycin resistance gene so that the plasmid can be selected in *E. coli*. Inserts such as the HCV core gene, are cloned into a polylinker region which places the insert between and operably linked to the promoter and polyadenylation signal. Transcription of the cloned inserts is under the control of the CMV promoter and the RSV enhancer elements. A polyadenylation signal is provided by the presence of an SV40 poly A signal situated just 3' of the cloning site.

What is claimed is:

1. A recombinant DNA molecule comprising a nucleotide coding sequence that encodes a fusion protein, wherein said fusion protein consists of a hepatitis B virus S gene product linked to amino acids 1–69 of the hepatitis C virus core protein.

2. The recombinant nucleic acid molecule of claim 1 wherein the N terminal amino acid of said hepatitis C virus core protein is linked to the C terminal amino acid of said hepatitis B virus S gene product.

3. A method of inducing an immune response against hepatitis C virus in an individual uninfected by hepatitis C virus comprising the step of:
    administering to said individual the DNA molecule of claim 1 in an amount effective to induce an immune response against hepatitis C virus.

4. A method of treating an individual who is infected with the hepatitis C virus comprising the step of:

administering to said individual the DNA molecule of claim 1 in an amount effective to induce an immune response against hepatitis C virus, wherein antibodies are produced.

5. A recombinant DNA molecule comprising a nucleotide sequence that encodes a fusion protein, wherein said fusion protein consists of a hepatitis B virus S gene product linked to amino acids 1–70 to 1–154 of the hepatitis C virus core protein.

6. The recombinant nucleic acid molecule of claim 5 wherein the N terminal amino acid of said hepatitis C virus core protein is linked to the C terminal amino acid of said hepatitis B virus S gene product.

7. A method of inducing an immune response against hepatitis C virus in an individual uninfected by hepatitis C virus comprising the step of:

administering to said individual the DNA molecule of claim 5 in an amount effective to induce an immune response against hepatitis C virus.

8. A method of treating an individual who is infected with hepatitis C virus comprising the step of:

administering to said individual the DNA molecule of claim 5 in an amount effective to induce an immune response against hepatitis C virus, wherein antibodies are produced.

9. A recombinant DNA molecule comprising a nucleotide sequence that encodes a fusion protein, wherein said fusion protein consists of a fragment of the hepatitis B virus pre S2 gene product linked to the hepatitis B virus S gene product linked to amino acids 1–69 of the hepatitis C virus core protein.

10. The recombinant nucleic acid molecule of claim 9 wherein the N terminal amino acid of said hepatitis B virus S gene product is linked to the C terminal amino acid of said hepatitis B virus pre S2 gene product, and the N terminal amino acid of said hepatitis C virus core protein is linked to the C terminal amino acid of said hepatitis B virus S gene product.

11. A method of inducing an immune response against hepatitis C virus in an individual uninfected by hepatitis C virus comprising the step of:

administering to said individual the DNA molecule of claim 9 in an amount effective to induce an immune response against hepatitis C virus.

12. A method of treating an individual who is infected with hepatitis C virus comprising the step of:

administering to said individual the DNA molecule of claim 9 in an amount effective to induce an immune response against hepatitis C virus, wherein antibodies are produced.

13. A recombinant DNA molecule comprising a nucleotide sequence that encodes a fusion protein, wherein said fusion protein consists of a fragment of the hepatitis B virus pre S2 gene product linked to the hepatitis B virus S gene product linked to amino acids 1–70 to 1–154 of the hepatitis C virus core protein.

14. The recombinant nucleic acid molecule of claim 13 wherein the N terminal amino acid of said hepatitis B virus S gene product is linked to the C terminal amino acid of said hepatitis B virus pre S2 gene product, and the N terminal amino acid of said hepatitis C virus core protein is linked to the C terminal amino acid of said hepatitis B virus S gene product.

15. A method of inducing an immune response against hepatitis C virus in an individual uninfected by hepatitis C virus comprising the step of:

administering to said individual the DNA molecule of claim 13 in an amount effective to induce an immune response against hepatitis C virus.

16. A method of treating an individual who is infected with hepatitis C virus comprising the step of:

administering to said individual the DNA molecule of claim 13 in an amount effective to induce an immune response against hepatitis C virus, wherein antibodies are produced.

17. A recombinant DNA molecule comprising a nucleotide sequence that encodes a fusion protein, wherein said fusion protein consists of the hepatitis B virus pre S2 gene product linked to the hepatitis B virus S gene product linked to amino acids 1–69 of the hepatitis C virus core protein.

18. The recombinant nucleic acid molecule of claim 17 wherein the N terminal amino acid of said hepatitis B virus S gene product is linked to the C terminal amino acid of said hepatitis B virus pre S2 gene product, and the N terminal amino acid of said hepatitis C virus core protein is linked to the C terminal amino acid of said hepatitis B virus S gene product.

19. A method of immunizing an individual susceptible to or infected by hepatitis C virus for producing antibodies comprising the step of:
administering to said individual the DNA molecule of claim 17 in an amount effective to induce an immune response, wherein antibodies are produced.

20. A method of treating an individual who is infected with hepatitis C virus comprising the step of:
administering to said individual the DNA molecule of claim 17 in an amount effective to induce an immune response against hepatitis C virus, wherein antibodies are produced.

21. A recombinant DNA molecule comprising a nucleotide sequence that encodes a fusion protein, wherein said fusion protein consists of the hepatitis B virus pre S2 gene product linked to the hepatitis B virus S gene product linked to amino acids 1–70 to 1–154 of the hepatitis C virus core protein.

22. The recombinant nucleic acid molecule of claim 21 wherein the N terminal amino acid of said hepatitis B virus S gene product is linked to the C terminal amino acid of said hepatitis B virus pre S2 gene product, and the N terminal amino acid of said hepatitis C virus core protein is linked to the C terminal amino acid of said hepatitis B virus S gene product.

23. A method of immunizing an individual susceptible to or infected by hepatitis C virus for producing antibodies comprising the step of:
administering to said individual the DNA molecule of claim 21 in an amount effective to induce an immune response, wherein antibodies are produced.

24. A method of treating an individual who is infected with hepatitis C virus comprising the step of:
administering to said individual the DNA molecule of claim 21 in an amount effective to induce an immune response against hepatitis C virus, wherein antibodies are produced.

25. The recombinant DNA molecule of any one of claims 1, 5, 9, 13, 17, or 21 comprising a cytomegalovirus promoter, a Rous Sarcoma Virus enhancer, and a polyadenylation sequence, wherein the nucleotide coding sequence is operatively linked to said promoter, enhancer, and polyadenylation sequence.

26. The recombinant DNA molecule of claim 25 further comprising the 5' UTR of hepatitis C virus, wherein said nucleotide coding sequence is operatively linked thereto.

27. A recombinant DNA molecule comprising a nucleotide coding sequence that encodes a fusion protein, wherein said fusion protein is selected from the group consisting of: a fusion protein that consists of the hepatitis B virus S gene product linked to a truncated hepatitis C virus core protein, a fusion protein that consists of a fragment of the the hepatitis B virus pre S2 gene product linked to the hepatitis B virus S gene product linked to a truncated hepatitis C virus core protein, and a fusion protein that consists of the hepatitis B virus pre S2 gene product linked to the hepatitis B virus S gene product linked to a truncated hepatitis C virus core protein.

28. The recombinant DNA molecule of claim 27 wherein said fusion protein consists of the hepatitis B virus S gene product linked to a truncated hepatitis C virus core protein.

29. The recombinant DNA molecule of claim 27 wherein said fusion protein consists of a fragment of the hepatitis B virus pre S2 gene product linked to the hepatitis B virus S gene product linked to a truncated hepatitis C virus core protein.

30. The recombinant DNA molecule of claim 27 wherein said fusion protein consists of the hepatitis B virus pre S2 gene product linked to the hepatitis B virus S gene product linked to a truncated hepatitis C virus core protein.

31. A pharmaceutical composition comprising:
a) a recombinant DNA molecule of claim 1; wherein said nucleotide sequence is operably linked to regulatory elements functional in human cells; and
b) a pharmaceutically acceptable carrier or diluent.

32. The pharmaceutical composition of claim 31 wherein said regulatory elements functional in human cells comprise a cytomegalovirus promoter, a Rous Sarcoma Virus enhancer, a polyadenylation sequence.

33. The pharmaceutical composition of claim 32 further comprising the 5' UTR of hepatitis C virus.

34. A method of immunizing an individual susceptible to or infected by hepatitis C virus for producing antibodies comprising the step of:
administering to said individual the pharmaceutical composition of claim 31 in an amount effective to induce an immune response, wherein antibodies are produced.

35. The method of claim 34 wherein bupivacaine is administered to said individual at the site of administration of the pharmaceutical composition.

36. A pharmaceutical composition comprising:
a) the recombinant DNA molecule of claim 5, wherein said nucleotide sequence is operably linked to regulatory elements functional in human cells; and
b) a pharmaceutically acceptable carrier or diluent.

37. The pharmaceutical composition of claim 36 wherein said regulatory elements functional in human cells comprise a cytomegalovirus promoter, a Rous Sarcoma Virus enhancer, a polyadenylation sequence.

38. The pharmaceutical composition of claim 37 further comprising the 5' UTR of hepatitis C virus.

39. A method of immunizing an individual susceptible to or infected by hepatitis C virus for producing antibodies comprising the step of:
administering to said individual the pharmaceutical composition of claim 36 in an amount effective to induce an immune response, wherein antibodies are produced.

40. The method of claim 39 wherein bupivacaine is administered to said individual at the site of administration of the pharmaceutical composition.

41. A pharmaceutical composition comprising:
a) the recombinant DNA molecule of claim 9, wherein said nucleotide sequence is operably linked to regulatory elements functional in human cells; and
b) a pharmaceutically acceptable carrier or diluent.

42. The pharmaceutical composition of claim 41 wherein said regulatory elements functional in human cells comprise a cytomegalovirus promoter, a Rous Sarcoma Virus enhancer, a polyadenylation sequence.

43. The pharmaceutical composition of claim 42 further comprising the 5' UTR of hepatitis C virus.

44. A method of immunizing an individual susceptible to or infected by hepatitis C virus for producing antibodies comprising the step of:

administering to said individual the pharmaceutical composition of claim 41 in an amount effective to induce an immune response, wherein antibodies are produced.

45. The method of claim 44 wherein bupivacaine is administered to said individual at the site of administration of the pharmaceutical composition.

46. A pharmaceutical composition comprising:

a) the recombinant DNA molecule of claim 13, wherein said nucleotide sequence is operably linked to regulatory elements functional in human cells; and b) a pharmaceutically acceptable carrier or diluent.

47. The pharmaceutical composition of claim 46 wherein said regulatory elements functional in human cells comprise a cytomegalovirus promoter, a Rous Sarcoma Virus enhancer, a polyadenylation sequence.

48. The pharmaceutical composition of claim 47 further comprising the 5' UTR of hepatitis C virus.

49. A method of immunizing an individual susceptible to or infected by hepatitis C virus for producing antibodies comprising the step of:

administering to said individual the pharmaceutical composition of claim 46 in an amount effective to induce an immune response, wherein antibodies are produced.

50. The method of claim 49 wherein bupivacaine is administered to said individual at the site of administration of the pharmaceutical composition.

51. A pharmaceutical composition comprising:

a) the recombinant DNA molecule of claim 17, wherein said nucleotide sequence is operably linked to regulatory elements functional in human cells; and b) a pharmaceutically acceptable carrier or diluent.

52. The pharmaceutical composition of claim 51 wherein said regulatory elements functional in human cells comprise a cytomegalovirus promoter, a Rous Sarcoma Virus enhancer, a polyadenylation sequence.

53. The pharmaceutical composition of claim 52 further comprising the 5' UTR of hepatitis C virus.

54. A method of immunizing an individual susceptible to or infected by hepatitis C virus for producing antibodies comprising the step of:

administering to said individual the pharmaceutical composition of claim 51 in an amount effective to induce an immune response, wherein antibodies are produced.

55. The method of claim 54 wherein bupivacaine is administered to said individual at the site of administration of the pharmaceutical composition.

56. A pharmaceutical composition comprising:

a) the recombinant DNA molecule of claim 21, wherein said nucleotide sequence is operably linked to regulatory elements functional in human cells; and b) a pharmaceutically acceptable carrier or diluent.

57. The pharmaceutical composition of claim 56 wherein said regulatory elements functional in human cells comprise a cytomegalovirus promoter, a Rous Sarcoma Virus enhancer, a polyadenylation sequence.

58. The pharmaceutical composition of claim 57 further comprising the 5' UTR of hepatitis C virus.

59. A method of immunizing an individual susceptible to or infected by hepatitis C virus for producing antibodies comprising the step of:

administering to said individual the pharmaceutical composition of claim 56 in an amount effective to induce an immune response, wherein antibodies are produced.

60. The method of claim 59 wherein bupivacaine is administered to said individual at the site of administration of the pharmaceutical composition.

* * * * *

UNITED STATES PATENT AND TRADEMARK OFFICE
CERTIFICATE OF CORRECTION

PATENT NO. : 6,025,341
DATED : February 15, 2000
INVENTOR(S) : Wands et al.

It is certified that error appears in the above-indentified patent and that said Letters Patent is hereby corrected as shown below:

Col. 12, line 60, please delete "April 14, 1994" and insert therefor --April 1, 1994--.

Col. 3, line 31, please delete "IFN-A" and insert therefor --IFN-α--.

Col. 4, line 20, please delete "800%" and insert therefor --80%--.

Signed and Sealed this

Fifteenth Day of May, 2001

*Attest:*

NICHOLAS P. GODICI

*Attesting Officer*   *Acting Director of the United States Patent and Trademark Office*